(12) United States Patent
Kim et al.

(10) Patent No.: US 10,370,676 B2
(45) Date of Patent: Aug. 6, 2019

(54) GENES RELATED TO SALT OR DROUGHT STRESS RESISTANCES AND TRANSFORMED PLANTS WITH THE SAME

(71) Applicant: INDUSTRY-ACADEMIC COOPERATION FOUNDATION, YONSEI UNIVERSITY, Seoul (KR)

(72) Inventors: Woo Taek Kim, Gyeonggi-do (KR); Jae Hwan Hwang, Seoul (KR); Dong Hye Seo, Gyeonggi-do (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 657 days.

(21) Appl. No.: 14/327,905

(22) Filed: Jul. 10, 2014

(65) Prior Publication Data
US 2015/0121571 A1 Apr. 30, 2015

(30) Foreign Application Priority Data
Oct. 24, 2013 (KR) .................. 10-2013-0127073

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01)

(58) Field of Classification Search
None
See application file for complete search history.

(56) References Cited

U.S. PATENT DOCUMENTS

| 7,214,786 | B2 | 5/2007 | Kovalic et al. |
| 7,612,177 | B2 | 11/2009 | Mulet salort et al. |
| 2012/0278944 | A1 | 11/2012 | Wang et al. |

OTHER PUBLICATIONS

*Arabidopsis thaliana* T-DNA line SALK_012549, published Oct. 8, 2009.*
Cho et al., 2008, The Plant Cell 20: 1899-1914.*
Tester and Bacic, 2005, Plant Physiology 137: 791-793.*
Zhu, 2002, Annu. Rev. Plant Biol. 53: 247-273.*
SALK *Arabidopsis* T-DNA 2010 information, available at http://signal.salk.edu/.*

* cited by examiner

*Primary Examiner* — Bratislav Stankovic
(74) *Attorney, Agent, or Firm* — Harness, Dickey & Pierce, P.L.C.

(57) ABSTRACT

The present invention relates to a composition for improving a tolerance to a salt stress or a drought stress of a plant, and a method for preparing transformed plant exhibiting improved tolerance to salt stress or drought stress. The nucleotide sequences of the present invention are involved in salt or drought stress-tolerance, therefore may be effectively used for cultivating the plants with novel functional features which are less affected by climates and environments of the cultivated areas.

6 Claims, 6 Drawing Sheets
Specification includes a Sequence Listing.

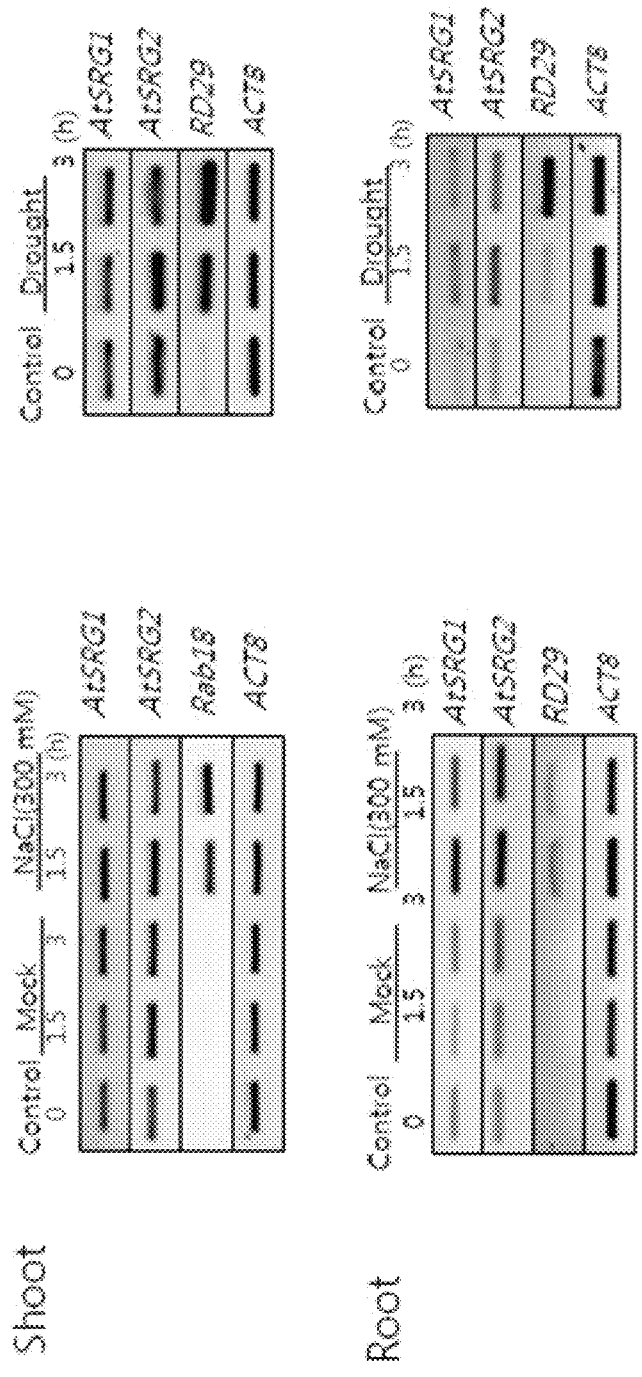

Fig. 3a
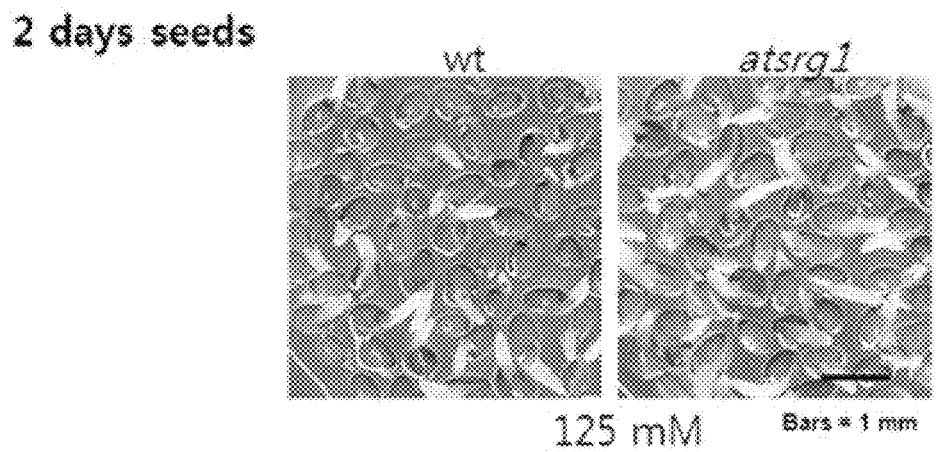
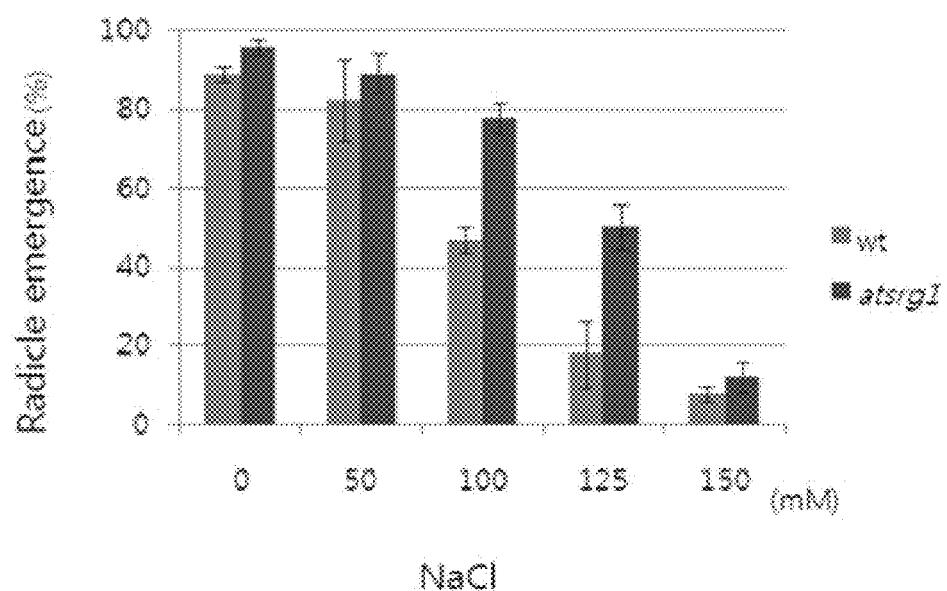

Fig. 3b
4 days seedlings
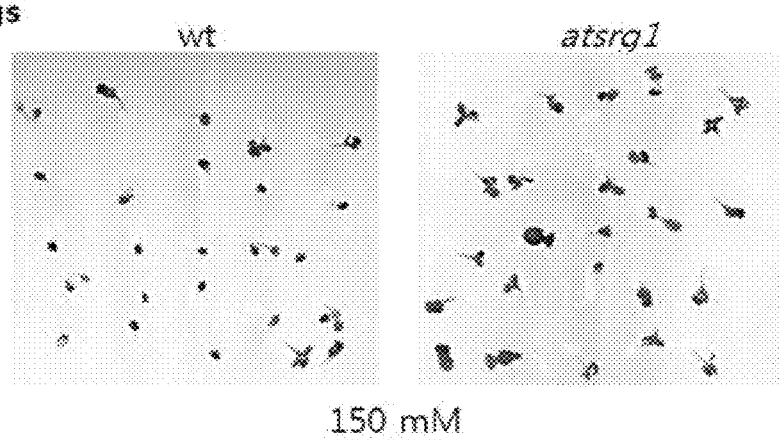
150 mM
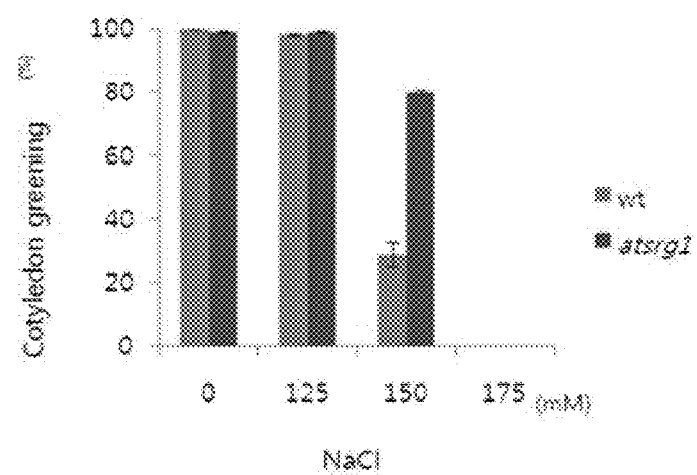

7 days seedling    Wt    *atsrg1*

150 mM

4 weeks plant    Wt    *atsrg1*

125 mM 5 weeks plants salt stress treated

SEQUENCE LISTING

<160> NUMBER OF SEQ ID NOS: 15

<210> SEQ ID NO 1
<211> LENGTH: 1347
<212> TYPE: DNA
<213> ORGANISM: Arabidopsis thaliana

<400> SEQUENCE: 1

| | | | | | | |
|---|---|---|---|---|---|---|
| atgccgatgt | ttcagccgtt | aaagagagat | gggttaatag | gatttgaagg | tggtggtgat | 60 |
| gggcaagtct | tagatctgga | tactgcagtg | aaagatggag | ttctcggtgg | tgttaatggt | 120 |
| ggtggtgttg | gagttgttga | tgagaaattg | gatctgaaga | agatgataaa | ggagctagat | 180 |
| ttacaagata | taccttctgt | tttcatttgt | cctatctcct | tagagccgat | gcaagatcct | 240 |
| gtgactttgt | gtactggtca | aacctatgaa | aggttaaaca | ttcacaaatg | gtttaaccta | 300 |
| ggtcacttga | cttgtcctac | tacaatgcaa | gagctttggg | atgatacggt | aactcctaat | 360 |
| aaaactcttc | atcatttgat | ctatacttgg | ttctctcaga | gtatgtgtt | gatgaagaaa | 420 |
| cgttctgagg | atgttcaagg | acgagctatt | gagattttgg | ggactttgaa | gaaagctaaa | 480 |
| ggtcaagcta | gggttcatgc | tttgagtgag | cttaaacaga | ttgttattgc | tcatcttatg | 540 |
| gcgaggaaga | ctgttgttga | agaaggtggt | gtctctgtga | tctcttctct | tttgggtcct | 600 |
| tttacttctc | atgctgttgg | atctgaggtt | gttgctattc | ttgtgagtct | tgatcttgat | 660 |
| tctgattcga | atccggctt | gatgcaacca | gctaaggttt | ctttgattgt | tgatatgttg | 720 |
| aatgatggat | ctaatgagac | taagatcaat | tgtgctagat | tgattagagg | attggtggaa | 780 |
| gagaaagggt | ttagagcaga | gcttgtttca | agtcatagtt | tgcttgttgg | gttaatgaga | 840 |
| ttggttaagg | ataagagaca | tagaaatgga | gtatctcctg | cacttcggtt | gcttaaaccg | 900 |
| atttcggttc | ataaacaagt | tcgaagcttg | atggttagca | ttggagcagt | gcctcaatta | 960 |
| gttgatatct | taccgtcttt | agacccggaa | tgtttggagt | tagctctgtt | tgttcttgat | 1020 |
| gctttgtgta | cagacgtgga | aggaagagtt | gctgtcaaag | actctgcaaa | cacaatacct | 1080 |
| tatacagtta | gggtgctgat | gagggtgtct | gagaattgca | ctaactacgc | gctgtcgatt | 1140 |
| ctttggtctg | tctgcaaatt | agctccagaa | gaatgttcac | cacttgctgt | tgaggttggt | 1200 |
| cttgctgcaa | agctgttact | cgtgatccag | agcgggtgtg | atgcagcgtt | gaagcagcgg | 1260 |
| tcagcagagc | tacttaagct | ttgtagtcta | cattattcag | acaccatgtt | tatttccaaa | 1320 |
| tgcaaactca | caaggacaat | ccaatag | | | | 1347 |

<210> SEQ ID NO 2
<211> LENGTH: 1335
<212> TYPE: DNA
<213> ORGANISM: Arabidopsis thaliana

<400> SEQUENCE: 2

| | | | | | | |
|---|---|---|---|---|---|---|
| atgccaatgt | ttcagccttc | taagaacggt | gggtttgatg | gcatatctt | agatctacac | 60 |
| tcggcggtta | agacggtgt | tcttggcggc | ggagatggga | aatttctggt | ggttgttacc | 120 |
| gatgagaaga | agaaattgga | tttgaaggag | atgatttctg | agctggaatt | acctgaaata | 180 |
| ccctctgttt | tcatctgtcc | tatctctcta | gagccgatgc | aagatccagt | gaccttgtgt | 240 |
| actggtcaaa | cctacgagag | gtccaacatt | tcaaatggt | tcaatatagg | gcattgtact | 300 |
| tgcccaacga | cgatgcaaga | gctttgggat | gatttggtca | ctcctaacaa | gactcttcac | 360 |
| caattgatct | acacttggtt | ttcacagaag | tatgttttga | tgaagaaacg | atctgaagat | 420 |
| gtgcaaggac | gtgctattga | gattctgggt | acgttgagaa | aggctaaagg | gaaagcaaag | 480 |

-continued

```
gttcatgctt taagcgagct taagcaagtt gtgatggctc acgctattgc taagaagact    540
gttgttgatg aaggtggagt ctttgtgatc tcttctcttt taagtccttt tacttctcac    600
gctgttggat ctgaggctat agctattctt gttaatcttg agcttgactc tgattccaaa    660
gctggattga tgcaaccagc tagggtctcg ttgatggttg atatgttgaa tgatggttcg    720
attgaaacta agatcaattg tgctagattg attggaaggt tggtggagga gaaaggtttt    780
agagcagagc ttgtttctag tcatagtttg cttgttggat taatgagatt ggttaaagat    840
aggagacgaa gaaacggcgt tcgcctgcg ttaacgctgc tcaaatcggt ttctgttcat    900
aaacaagtta ggaacttgtt ggttaggatt ggtgcagttc ctcaattggt tgatgttttg    960
ccatgtttgg atgtggagtg tttagagtca gctcttttcg tgttggattc gttatgttta   1020
gaaagcgaag gcagaattgc tttgaaagat tcggttaaca cgattccgca taccgttagg   1080
ttactgatga aggtatcaga gaaatgcaca aactatgcga tatcgattct ttggtcagtt   1140
tgcaaattag cttctgaaga atgttcatct cttgctgttg aagttggttt ggctgcaaag   1200
cttttgcttg tgatacaaag tggatgtgat ccagctttga agcaacgttc agctgagcta   1260
ttgaagttat gtagtctaca ttattcagac tcaatgttta tctccaaatg taaactcaca   1320
agaactatcc aataa                                                    1335
```

<210> SEQ ID NO 3
<211> LENGTH: 448
<212> TYPE: PRT
<213> ORGANISM: Arabidopsis thaliana

<400> SEQUENCE: 3

```
Met Pro Met Phe Gln Pro Leu Lys Arg Asp Gly Leu Ile Gly Phe Glu
1               5                   10                  15

Gly Gly Gly Asp Gly Gln Val Leu Asp Leu Asp Thr Ala Val Lys Asp
            20                  25                  30

Gly Val Leu Gly Gly Val Asn Gly Gly Val Gly Val Val Asp Glu
        35                  40                  45

Lys Leu Asp Leu Lys Lys Met Ile Lys Glu Leu Asp Leu Gln Asp Ile
50                  55                  60

Pro Ser Val Phe Ile Cys Pro Ile Ser Leu Glu Pro Met Gln Asp Pro
65                  70                  75                  80

Val Thr Leu Cys Thr Gly Gln Thr Tyr Glu Arg Leu Asn Ile His Lys
                85                  90                  95

Trp Phe Asn Leu Gly His Leu Thr Cys Pro Thr Thr Met Gln Glu Leu
            100                 105                 110

Trp Asp Asp Thr Val Thr Pro Asn Lys Thr Leu His His Leu Ile Tyr
        115                 120                 125

Thr Trp Phe Ser Gln Lys Tyr Val Leu Met Lys Lys Arg Ser Glu Asp
    130                 135                 140

Val Gln Gly Arg Ala Ile Glu Ile Leu Gly Thr Leu Lys Lys Ala Lys
145                 150                 155                 160

Gly Gln Ala Arg Val His Ala Leu Ser Glu Leu Lys Gln Ile Val Ile
                165                 170                 175

Ala His Leu Met Ala Arg Lys Thr Val Val Glu Gly Gly Val Ser
            180                 185                 190

Val Ile Ser Ser Leu Leu Gly Pro Phe Thr Ser His Ala Val Gly Ser
        195                 200                 205

Glu Val Val Ala Ile Leu Val Ser Leu Asp Leu Asp Ser Asp Ser Lys
```

```
Ser Gly Leu Met Gln Pro Ala Lys Val Ser Leu Ile Val Asp Met Leu
225                 230                 235                 240

Asn Asp Gly Ser Asn Glu Thr Lys Ile Asn Cys Ala Arg Leu Ile Arg
                245                 250                 255

Gly Leu Val Glu Lys Gly Phe Arg Ala Glu Leu Val Ser Ser His
            260                 265                 270

Ser Leu Leu Val Gly Leu Met Arg Leu Val Lys Asp Lys Arg His Arg
        275                 280                 285

Asn Gly Val Ser Pro Ala Leu Arg Leu Lys Pro Ile Ser Val His
    290                 295                 300

Lys Gln Val Arg Ser Leu Met Val Ser Ile Gly Ala Val Pro Gln Leu
305                 310                 315                 320

Val Asp Ile Leu Pro Ser Leu Asp Pro Glu Cys Leu Glu Leu Ala Leu
                325                 330                 335

Phe Val Leu Asp Ala Leu Cys Thr Asp Val Glu Gly Arg Val Ala Val
            340                 345                 350

Lys Asp Ser Ala Asn Thr Ile Pro Tyr Thr Val Arg Val Leu Met Arg
        355                 360                 365

Val Ser Glu Asn Cys Thr Asn Tyr Ala Leu Ser Ile Leu Trp Ser Val
370                 375                 380

Cys Lys Leu Ala Pro Glu Glu Cys Ser Pro Leu Ala Val Glu Val Gly
385                 390                 395                 400

Leu Ala Ala Lys Leu Leu Leu Val Ile Gln Ser Gly Cys Asp Ala Ala
                405                 410                 415

Leu Lys Gln Arg Ser Ala Glu Leu Leu Lys Leu Cys Ser Leu His Tyr
            420                 425                 430

Ser Asp Thr Met Phe Ile Ser Lys Cys Lys Leu Thr Arg Thr Ile Gln
        435                 440                 445

<210> SEQ ID NO 4
<211> LENGTH: 444
<212> TYPE: PRT
<213> ORGANISM: Arabidopsis thaliana

<400> SEQUENCE: 4

Met Pro Met Phe Gln Pro Ser Lys Asn Gly Gly Phe Asp Gly His Ile
1               5                   10                  15

Leu Asp Leu His Ser Ala Val Lys Asp Gly Val Leu Gly Gly Gly Asp
                20                  25                  30

Gly Lys Phe Leu Val Val Thr Asp Glu Lys Lys Leu Asp Leu
            35                  40                  45

Lys Glu Met Ile Ser Glu Leu Glu Leu Pro Glu Ile Pro Ser Val Phe
50                  55                  60

Ile Cys Pro Ile Ser Leu Glu Pro Met Gln Asp Pro Val Thr Leu Cys
65                  70                  75                  80

Thr Gly Gln Thr Tyr Glu Arg Ser Asn Ile Leu Lys Trp Phe Asn Ile
                85                  90                  95

Gly His Cys Thr Cys Pro Thr Thr Met Gln Glu Leu Trp Asp Asp Leu
            100                 105                 110

Val Thr Pro Asn Lys Thr Leu His Gln Leu Ile Tyr Thr Trp Phe Ser
        115                 120                 125

Gln Lys Tyr Val Leu Met Lys Lys Arg Ser Glu Asp Val Gln Gly Arg
    130                 135                 140
```

```
Ala Ile Glu Ile Leu Gly Thr Leu Arg Lys Ala Lys Gly Lys Ala Lys
145                 150                 155                 160

Val His Ala Leu Ser Glu Leu Lys Gln Val Val Met Ala His Ala Ile
            165                 170                 175

Ala Lys Lys Thr Val Val Asp Glu Gly Gly Val Phe Val Ile Ser Ser
        180                 185                 190

Leu Leu Ser Pro Phe Thr Ser His Ala Val Gly Ser Glu Ala Ile Ala
    195                 200                 205

Ile Leu Val Asn Leu Glu Leu Asp Ser Asp Ser Lys Ala Gly Leu Met
210                 215                 220

Gln Pro Ala Arg Val Ser Leu Met Val Asp Met Leu Asn Asp Gly Ser
225                 230                 235                 240

Ile Glu Thr Lys Ile Asn Cys Ala Arg Leu Ile Gly Arg Leu Val Glu
            245                 250                 255

Glu Lys Gly Phe Arg Ala Glu Leu Val Ser Ser His Ser Leu Leu Val
        260                 265                 270

Gly Leu Met Arg Leu Val Lys Asp Arg Arg Arg Asn Gly Val Ser
    275                 280                 285

Pro Ala Leu Thr Leu Leu Lys Ser Val Ser Val His Lys Gln Val Arg
290                 295                 300

Asn Leu Leu Val Arg Ile Gly Ala Val Pro Gln Leu Val Asp Val Leu
305                 310                 315                 320

Pro Cys Leu Asp Val Glu Cys Leu Glu Ser Ala Leu Phe Val Leu Asp
            325                 330                 335

Ser Leu Cys Leu Glu Ser Glu Gly Arg Ile Ala Leu Lys Asp Ser Val
        340                 345                 350

Asn Thr Ile Pro His Thr Val Arg Leu Leu Met Lys Val Ser Glu Lys
            355                 360                 365

Cys Thr Asn Tyr Ala Ile Ser Ile Leu Trp Ser Val Cys Lys Leu Ala
        370                 375                 380

Ser Glu Glu Cys Ser Ser Leu Ala Val Glu Val Gly Leu Ala Ala Lys
385                 390                 395                 400

Leu Leu Leu Val Ile Gln Ser Gly Cys Asp Pro Ala Leu Lys Gln Arg
            405                 410                 415

Ser Ala Glu Leu Leu Lys Leu Cys Ser Leu His Tyr Ser Asp Ser Met
        420                 425                 430

Phe Ile Ser Lys Cys Lys Leu Thr Arg Thr Ile Gln
        435                 440
```

<210> SEQ ID NO 5
<211> LENGTH: 21
<212> TYPE: DNA
<213> ORGANISM: Artificial Sequence
<220> FEATURE:
<223> OTHER INFORMATION: AtSRG1 U3 FW primer

<400> SEQUENCE: 5
caagctaggg ttcatgcttt g                                          21

<210> SEQ ID NO 6
<211> LENGTH: 20
<212> TYPE: DNA
<213> ORGANISM: Artificial Sequence
<220> FEATURE:
<223> OTHER INFORMATION: AtSRG1 17 RV primer

<400> SEQUENCE: 6
cagacaccct catcagcacc                                            20

<210> SEQ ID NO 7
<211> LENGTH: 21
<212> TYPE: DNA
<213> ORGANISM: Artificial Sequence
<220> FEATURE:
<223> OTHER INFORMATION: AtSRG2 u5 FW primer

<400> SEQUENCE: 7
ggtcaaacct acgagaggtc c                                          21

<210> SEQ ID NO 8
<211> LENGTH: 20
<212> TYPE: DNA
<213> ORGANISM: Artificial Sequence
<220> FEATURE:
<223> OTHER INFORMATION: AtSRG2 20 RV primer

<400> SEQUENCE: 8
cgatttgagc agcgttaacg                                            20

<210> SEQ ID NO 9
<211> LENGTH: 20
<212> TYPE: DNA
<213> ORGANISM: Artificial Sequence
<220> FEATURE:
<223> OTHER INFORMATION: RD29a FW primer

<400> SEQUENCE: 9
caggtgaatc aggagttgtt                                            20

<210> SEQ ID NO 10
<211> LENGTH: 20
<212> TYPE: DNA
<213> ORGANISM: Artificial Sequence
<220> FEATURE:
<223> OTHER INFORMATION: RD29a RV primer

<400> SEQUENCE: 10
ccggaaattt atcctcttct                                            20

<210> SEQ ID NO 11
<211> LENGTH: 27
<212> TYPE: DNA
<213> ORGANISM: Artificial Sequence
<220> FEATURE:
<223> OTHER INFORMATION: EV136F Act8 FW primer

<400> SEQUENCE: 11
tactgattac ctcatgaaga tccttac                                    27

<210> SEQ ID NO 12
<211> LENGTH: 26
<212> TYPE: DNA
<213> ORGANISM: Artificial Sequence
<220> FEATURE:
<223> OTHER INFORMATION: EV137R Act8 RV primer

<400> SEQUENCE: 12
aaacgatgtc tctttagttt agaagc                                     26

<210> SEQ ID NO 13
<211> LENGTH: 21
<212> TYPE: DNA
<213> ORGANISM: Artificial Sequence

```
<220> FEATURE:
<223> OTHER INFORMATION: AtSRG1 u4 RW primer

<400> SEQUENCE: 13
tcccaatgct tattgcaaaa c                                              21

<210> SEQ ID NO 14
<211> LENGTH: 21
<212> TYPE: DNA
<213> ORGANISM: Artificial Sequence
<220> FEATURE:
<223> OTHER INFORMATION: AtSRG2 u6 RW primer

<400> SEQUENCE: 14
atccgttgtg tgattttgac c                                              21

<210> SEQ ID NO 15
<211> LENGTH: 22
<212> TYPE: DNA
<213> ORGANISM: Artificial Sequence
<220> FEATURE:
<223> OTHER INFORMATION: LBa1 boder primer

<400> SEQUENCE: 15
tggttcacgt agtgggccat cg                                             22
```

GENES RELATED TO SALT OR DROUGHT STRESS RESISTANCES AND TRANSFORMED PLANTS WITH THE SAME

CROSS-REFERENCE TO RELATED APPLICATION AND CLAIM OF PRIORITY

This application claims the benefit of Korean Patent Application No. 10-2013-0127073, filed on Oct. 24, 2013, in the Korean Intellectual Property Office, the disclosures of which are incorporated herein in their entirety by reference.

BACKGROUND

1. Field of the Invention

The present invention relates genes related to salt or drought stress resistances, transformed plants with the same, and methods for preparing thereof.

2. Background of Technique

Due to their sessile nature, higher plants are constantly faced with various adverse environmental factors, including drought, high salt, heavy metals, cold, heat shock, and ozone, during their whole life span. These abiotic stresses are a limiting factor for the growth and development of crop plants. Water deficiency causes dramatic reduction of crop production globally, and the decreasing availability of fresh water may pose a future threat to humans and higher plants. Plants have diverse defense strategies to enhance their tolerance to transient and long-term water shortages by triggering signaling network pathways and inducing stress-responsive genes. The cellular and genetic defense mechanisms in response to water stress have been widely documented (Shinozaki and Yamaguchi-Shinozaki, 2007). However, for stress tolerance or sensitivity, our knowledge concerning the biological functions of stress-related genes in higher plants is still rudimentary. Therefore, it is important to study the functions of stress responsive genes to increase the productivity and distribution of crop plants.

The present inventors identified and isolated genes AtSRG1 and AtSRG2 genes which are induced in response to high salt or dehydration in *Arabidopsis* plants, and analyzed phenotypes of knock-out mutants thereof.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY

The present inventors have made intensive studies to identify genes for improving a tolerance to a salt stress or a drought stress of a plant. As results, the present inventors have discovered that nucleotide sequences encoding the amino acid sequences of SEQ ID NO:3 and SEQ ID NO:4, concretely nucleotide sequences of SEQ ID NO:1 and 2, respectively, are related to the tolerance to said stresses and that a plant with enhanced stress tolerance may be obtained by suppressing the expression of said nucleotides.

Accordingly, it is an object of this invention to provide a composition for improving a tolerance to a salt stress or a drought stress of a plant.

It is another object of this invention to provide a plant cell or a plant exhibiting improved tolerance to a salt stress or a drought stress transformed with the composition according to this invention.

It is still another object of this invention to provide a method for preparing transformed plant exhibiting improved tolerance to salt stress or drought stress.

Other objects and advantages of the present invention will become apparent from the following detailed description together with the appended claims and drawings.

BRIEF DESCRIPTION OF THE DRAWINGS

FIG. 1 represents the expression patterns of AtSRG1 and AtSRG2 genes in response to salt and drought stress conditions. The expressions of AtSRG1 and AtSRG2 were analyzed by semi-quantative RT-PCR after the plants were subjected to high salt and dehydration. As results, mRNA expression levels in root tissue were increased in response to both of stresses with similar pattern, indicating that two genes may have functions complementary to each other.

As seen in FIG. 2*a*, T-DNA insertions were mapped on ORF of AtSRG1 and AtSRG2. The knock-out of these genes was verified by PCR amplification using the T-DNA border primer and primers annealing to sites upstream and downstream of the T-DNA insertion site. FIG. 2*b* shows the result of verification of knock-out in advance of loss of function study.

FIGS. 3*a*-3*d* represent the phenotypes of AtSRG1 knock-out mutants in response to high salt. For concrete approach to the physiological functions of AtSRG1 and AtSRG2 genes, the phenotype of AtSRG1 knock-out mutant were analyzed first.

FIG. 3*a* shows the images and graphs for wild-type and AtSRG1 knock-out mutant *Arabidopsis* grown on high salinity medium. It was revealed that the high salt-resistance was enhanced by loss of function of the gene, evidenced by more generations of radicles compared to those of wild-type. FIG. 3*b* shows the germination rate of wild-type and knock-out mutant from the emergence of radicles to the cotyledon stage. Larger number of plants with cotyledons was observed in mutant population, indicating that the high salt-resistance shown in radicle stage had been maintained until the cotyledon stage. FIG. 3*c* shows that the high salt-resistance in germination stage was continued to the root development stage. The mutant plants grown in 150 mM NaCl media had longer roots than those of wild type. Taken together, the results of FIGS. 3*a* and 3*b* demonstrate that the AtSRG1 knock-out mutant exhibits salt-tolerance during overall stages of early germination.

FIG. 3*d* shows that the high salt-resistance in germination stage was maintained after germination. Larger number of plants grown on high salinity medium survived 4 weeks after seedling, compared to wild-type plants.

As seen in FIG. 4, AtSRG2 knock-out mutant showed strong tolerance to a salt stress.

Figure 2A:
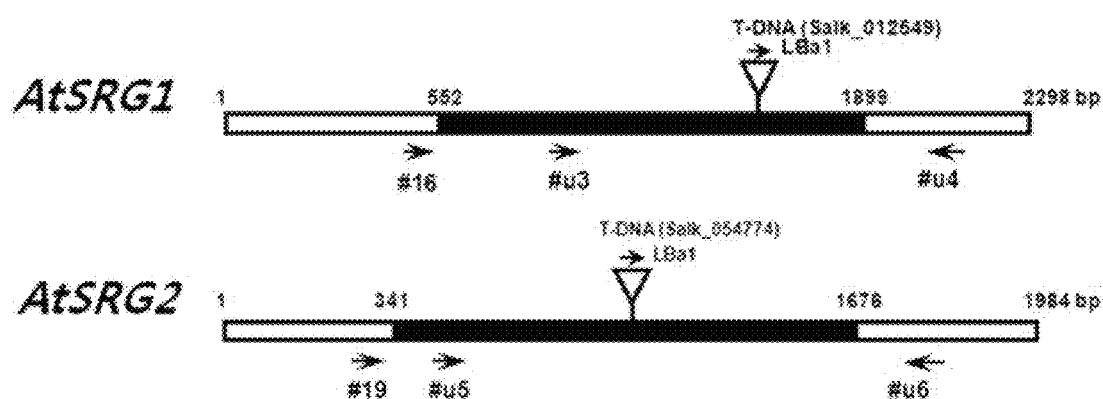
FIGS. 2*a* and 2*b* show the establishment of the AtSRG1 or AtSRG2 knock-out mutant. AtSRG1 and AtSRG2 knock-out mutants which are T-DNA insertion lines were purchased from ABRC, and confirmed by genotyping PCR and RT-PCR.
Figure 2B:
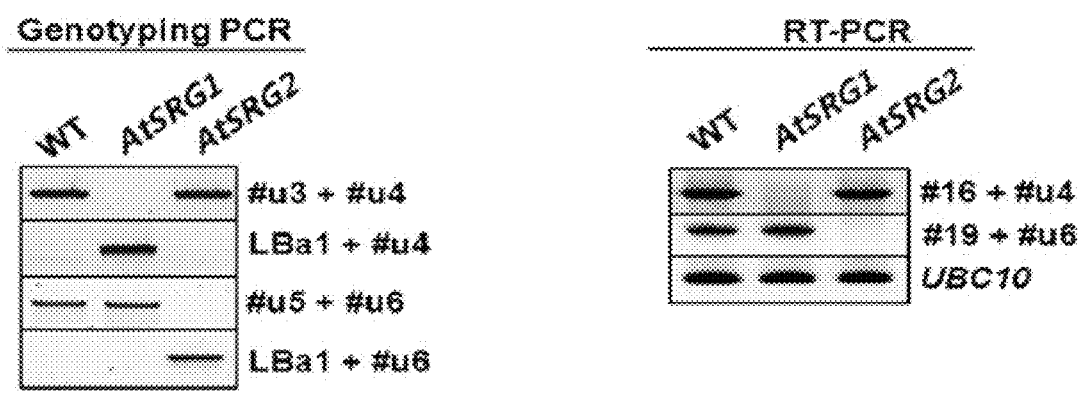
Figure 3C:
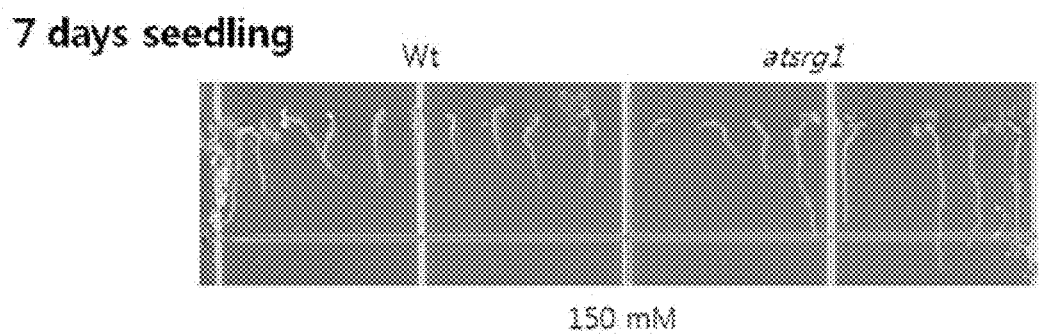
Figure 3D:
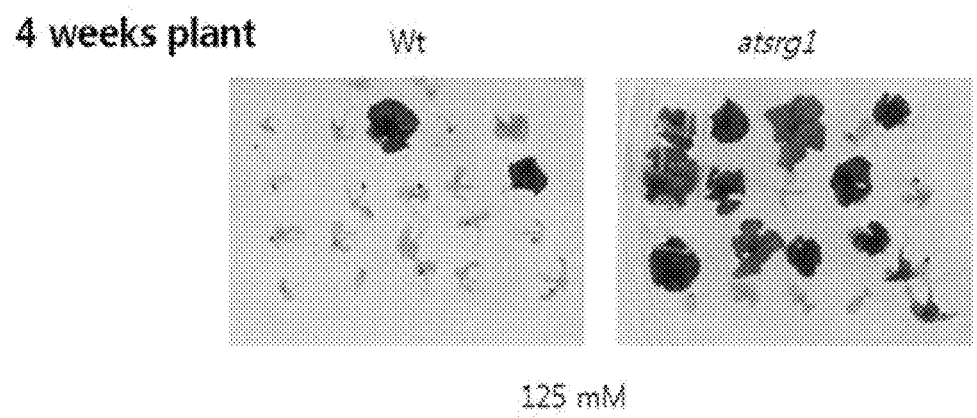

Taken together, the results of FIGS. 3*a*-3*d* and FIG. 4 demonstrate that the AtSRG1 and AtSRG2 genes are involved in the response to a salt stress at early stages of germination and at green plants, respectively.

DETAILED DESCRIPTION

In one aspect of this invention, there is provided a composition for improving a tolerance to a salt stress or a drought stress of a plant, comprising a nucleic acid molecule which inhibits an expression of a nucleotide sequence encoding the amino acid sequence selected from the group consisting of SEQ ID NO:3, SEQ ID NO:4 and the combination thereof.

The present inventors have made intensive studies to identify genes for improving a tolerance to a salt stress or a drought stress of a plant. As results, the present inventors have discovered that nucleotide sequences encoding the amino acid sequences of SEQ ID NO:3 and SEQ ID NO:4, concretely nucleotide sequences of SEQ ID NO:1 and 2, respectively, are related to the tolerance to said stresses and that a plant with enhanced stress tolerance may be obtained by suppressing the expression of said nucleotides.

According to the present invention, SEQ ID NOs:1 and 2 are the nucleotide sequences of AtSRG1 (At3g49810) and AtSRG2 (At5g65920) genes, respectively.

It would be obvious to the skilled artisan that the nucleotide sequences used in this invention are not limited to those listed in the appended Sequence Listings. For nucleotides, the variations may be purely genetic, i.e., ones that do not result in changes in the protein product. This includes nucleic acids that contain functionally equivalent codons, or codons that encode the same amino acid, such as six codons for arginine or serine, or codons that encode biologically equivalent amino acids.

Considering biologically equivalent variations described hereinabove, the nucleic acid molecule of this invention may encompass sequences having substantial identity to them. Sequences having the substantial identity show at least 60%, more concretely at least 70%, even more concretely at least 80%, and most concretely at least 90% similarity to the nucleic acid molecule of this invention, as measured using one of the sequence comparison algorithms. Methods of alignment of sequences for comparison are well-known in the art. Various programs and alignment algorithms are described in: Smith and Waterman, *Adv. Appl. Math.* 2:482 (1981); Needleman and Wunsch, *J. Mol. Bio.* 48:443(1970); Pearson and Lipman, *Methods in Mol. Biol* 24: 307-31 (1988); Higgins and Sharp, *Gene* 73:237-44(1988); Higgins and Sharp, *CABIOS* 5:151-3(1989) Corpet et al.,*Nuc. Acids Res.* 16:10881-90(1988) Huang et al., *Comp. Appl. BioSci* 8:155-65(1992) and Pearson et al., *Meth. Mol. Biol.* 24:307-31(1994). The NCBI Basic Local Alignment Search Tool (BLAST®) [Altschul et al., *J. Mol. Biol.* 215:403-10(1990)] is available from several sources, including the National Center for Biological Information (NBCl, Bethesda, Md.) and on the Internet, for use in connection with the sequence analysis programs blastp, blasm, blastx, tblastn and tblastx. It can be accessed at www.ncbi.nlm.nih.gov/BLAST/. A description of how to determine sequence identity using this program is available at www.ncbi.nlm.nih.gov/BLAST/blast_help.html.

According to the present invention, salt and drought stresses induce the expressions of AtSRG1 and AtSRG2 genes in plants, and inhibition of these genes confers enhanced tolerance to said stresses.

According to a concrete embodiment, the nucleotide sequence encoding the amino acid sequence of SEQ ID NO:3 is the nucleotide sequence of SEQ ID NO:1.

According to a concrete embodiment, the nucleotide sequence encoding the amino acid sequence of SEQ ID NO:4 is the nucleotide sequence of SEQ ID NO:2.

According to another concrete embodiment, the combinations of nucleotide sequences encoding the amino acid sequence of SEQ ID NO:3 and SEQ ID NO:4 confer a salt or a drought stress tolerance during overall period since germination to mature plant stage. The term "mature plant stage" as used herein refers to a stage when seedling establishment has been accomplished after seed germination.

According to a concrete embodiment, the nucleic acid molecule is T-DNA, siRNA, shRNA, miRNA, ribozyme, PNA (peptide nucleic acids) or antisense oligonucleotide. More concretely, the present nucleic acid molecule is T-DNA.

The term "siRNA" as used herein refers to a short double strand RNA that enables to mediate RNA interference via cleavage of mRNA. The siRNA of the present invention may consist of a sense RNA strand having a sequence corresponding to a target gene and an antisense RNA strand having a sequence complementary to the target gene. The siRNA to inhibit expression of a target gene provides effective gene knock-down method or gene therapy method.

The siRNA of this invention is not restricted to a RNA duplex of which two strands are completely paired and may comprise non-paired portion such as mismatched portion with non-complementary bases and bulge with no opposite bases. The overall length of the siRNA is 10-100 nucleotides, preferably 15-80 nucleotides, and more preferably, 20-70 nucleotides. The siRNA may comprise either blunt or cohesive end so long as it enables to inhibit the target gene expression via RNAi effect. The cohesive end may be prepared in 3'-end overhanging structure or 5'-end overhanging structure. The base number protruded is not particularly limited, for example 1-8 bases, preferably 2-6 bases. In addition, siRNA may comprise low molecular weight RNA (for example, tRNA, rRNA, natural RNA molecule such as viral RNA or artificial RNA molecule) in the protruded portion of one end to the extent that it enables to maintain an effect on the inhibition of target gene expression. The terminal structure of siRNA is not demanded as cut structure at both ends, and one end portion of double strand RNA may be stem-and-loop structure linked by a linker RNA. The length of linker is not restricted where it has no influence on the pair formation of the stem portion.

The term "shRNA" as used herein refers to a single strand nucleotide consisting of 50-70 bases, and forms stem-loop structure in vivo. Long RNA of 19-29 nucleotides is complementarily base-paired at both directions of loop consisting of 5-10 nucleotides, forming a double-stranded stem.

The term "miRNA (microRNA)" as used herein refers to a single strand nucleotide that functions to regulate gene expression and means a single strand RNA molecule composed of 20-50 nucleotides in full-length, preferably 20-45 nucleotides, more preferably 20-40 nucleotides, much more preferably 20-30 nucleotides and most preferably, 21-23 nucleotides. The miRNA is an oligonucleotide which is not expressed intracellularly, and forms a short stem-loop structure. The miRNA has a whole or partial complementarity to one or two or more mRNAs (messenger RNAs), and the target gene expression is suppressed by the complementary binding of miRNA to the mRNA thereof.

The term "ribozyme" as used herein refers to a RNA molecule having an activity of an enzyme in itself which recognizes and restricts a base sequence of a specific RNA. The ribozyme consists of a binding portion capable of specifically binding a base sequence complementary to a transfer RNA strand and an enzymatic portion to cut target RNA.

The term "PNA (peptide nucleic acid)" as used herein refers to a molecule having the characteristics of both nucleic acid and protein, which is capable of complementarily binding to DNA or RNA. PNA was first reported in 1999 as similar DNA in which nucleobases are linked via a peptide bond (Nielsen P E, Egholm M, Berg R H, Buchardt O, "Sequence-selective recognition of DNA by strand displacement with a thymine-substituted polyamide", Science 1991, Vol. 254: pp 1497-1500). PNA is absent in the natural world and artificially synthesized through a chemical method. PNA is reacted with a natural nucleic acid having a complementary base sequence through hybridization response, forming double strand. In the double strand with the same length, PNA/DNA and PNA/RNA double strand are more stable than DNA/DNA and DNA/RNA double strand, respectively. The form of repeating N-(2-aminoethyl)-glycine units linked by amide bonds is commonly used as a basic peptide backbone. In this context, the backbone of peptide nucleic acid is electrically neutral in comparison to that of natural nucleic acids having negative charge. Four bases of nucleic acid present in PNA are almost the same to those of natural nucleic acid in the respect of spatial size and distance between nucleobases. PNA has not only a chemical stability compared with natural nucleic acid, but also a biological stability due to no degradation by a nuclease or protease.

The term "antisense oligonucleotide" as used herein is intended to refer to nucleic acids, preferably, DNA, RNA or its derivatives, that are complementary to the base sequences of a target mRNA, characterized in that they bind to the target mRNA and interfere its translation to protein. The antisense oligonucleotide of the present invention refers to DNA or RNA sequences which are complementary to a target mRNA, characterized in that they bind to the target mRNA and interfere its translation to protein, translocation into cytoplasm, maturation or essential activities to other biological functions. The length of antisense nucleic acids is in a range of 6-100 nucleotides and preferably 10-40 nucleotides. The antisense oligonucleotides may be modified at above one or more positions of base, sugar or backbone to enhance their functions [De Mesmaeker, et al., *Curr Opin Struct Biol.*, 5(3): 343-55 (1995)]. The oligonucleotide backbone may be modified with phosphothioate, phosphotriester, methyl phosphonate, single chain alkyl, cycloalkyl, single chain heteroatomic, heterocyclic bond between sugars, and so on. In addition, the antisense nucleic acids may include one or more substituted sugar moieties. The antisense oligonucleotides may include a modified base. The modified base includes hypoxanthine, 6-methyladenine, 5-me pyrimidine (particularly, 5-methylcytosine), 5-hydroxymethylcytosine (HMC), glycosyl HMC, gentobiosyl HMC, 2-aminoadenine, 2-thiouracil, 2-thiothymine, 5-bromouracil, 5-hydroxymethyluracil, 8-azaguanine, 7-deazaguanine, N6(6-aminohexyl)adenine, 2,6-diaminopurine, and so forth.

The term "T-DNA" as used herein refers to a DNA fragment as a transfer DNA in Ti (tumor-inducing) plasmid of *Agrobacterium* sp., which is transferred into a nucleus of a host plant cell. A 25 bp repeat sequence is present in both termini of T-DNA, and DNA transfer proceeds at the direction from a left border to a right border. A bacterial T-DNA with about 20,000 in length destroys a target gene by insertion, resulting in insertional muatagenesis. In addition to mutation, inserted T-DNA sequence may label a target gene. The mutant plants in which AtSRG1 or AtSRG2 expression is suppressed by way of T-DNA insertions (seed number: AtSRG1—salk_012549, AtSRG2—salk_054774) were purchased from SIGNAL Salk Institute Genomuc Analysis Laboratory (http://signal.salk.edu/)

In another aspect of this invention, there is provided a plant cell exhibiting improved tolerance to a salt stress or a drought stress, transformed with the composition of this invention.

In still another aspect of this invention, there is provided a plant exhibiting improved tolerance to a salt stress or a drought stress, transformed with the composition of this invention.

Introducing a foreign nucleotide sequence into plant cells or plants may be performed by the methods (*Methods of Enzymology*, Vol. 153, 1987) known to those skilled in the art. The plant may be transformed using the foreign nucleotide inserted into a carrier (e.g., vectors such as plasmid or virus) or *Agrobacterium tumefaciens* as a mediator (Chilton et al., *Cell,* 11: 263-271 (1977)) and by directly inserting the foreign nucleotide into plant cells (Lorz et al., *Mol. Genet.*, 199: 178-182 (1985); the disclosure is herein incorporated by reference). For example, electroporation, microparticle bombardment, polyethylene glycol-mediated uptake may be used in the vector containing no T-DNA region.

Generally, *Agrobacterium*-mediated transformation is the most preferable (U.S. Pat. Nos. 5,004,863, 5,349,124 and 5,416,011), and the skilled artisan can incubate or culture the transformed cells or seeds to mature plants in appropriate conditions.

The term "plant(s)" as used herein, is understood by a meaning including a plant cell, a plant tissue and a plant seed as well as a mature plant.

The plants applicable of the present method include, but not limited to, most dicotyledonous plants including lettuce, chinese cabbage, potato and radish, and most monocotyledonous plants including rice plant, barley and banana tree. Preferably, the present method can be applied to the plants selected from the group consisting of food crops such as rice plant, wheat, barley, corn, bean, potato, Indian bean, oat and Indian millet; vegetable crops such as *Arabidopsis* sp., Chinese cabbage, radish, red pepper, strawberry, tomato, watermelon, cucumber, cabbage, melon, pumpkin, welsh onion, onion and carrot; crops for special use such as ginseng, tobacco plant, cotton plant, sesame, sugar cane, sugar beet, *Perilla* sp., peanut and rape; fruit trees such as apple tree, pear tree, jujube tree, peach tree, kiwi fruit tree, grape tree, citrus fruit tree, persimmon tree, plum tree, apricot tree and banana tree; flowering crops such as rose, gladiolus, gerbera, carnation, chrysanthemum, lily and tulip; and fodder crops such as ryegrass, red clover, orchardgrass, alfalfa, tallfescue and perennial ryograss.

In still another aspect of this invention, there is provided a method for preparing transformed plant exhibiting improved tolerance to salt stress or drought stress, comprising:

(a) introducing the composition of this invention into a plant cell; and (b) obtaining the transformed plant exhibiting improved drought stress tolerance from the plant cell of (a).

Introducing a foreign gene into a plant cell via gene delivery systems such as plant expressing recombinant vectors can be carried out by various methods known to those skilled in the art. Selection of the transformed plant cell can be performed by exposing it to selective agents (e.g., metabolic inhibitors, antibiotics or herbicides). Transformed plant cells stably harboring marker genes which give a tolerance to selective agents are grown and divided in above culture.

The exemplary markers include, but not limited to, hygromycin phosphotransferase (hpt), glyphosate-resistance gene and neomycin phophotransferase (nptII) system.

The methods for developing or regenerating plants from plant protoplasms or various ex-plants are well known to those skilled in the art. The development or regeneration of plants containing the foreign gene of interest introduced by *Agrobacterium* may be achieved by methods well known in the art (U.S. Pat. Nos. 5,004,863, 5,349,124 and 5,416,011).

According to a concrete embodiment, the plant of this invention is selected from the group consisting of food crops such as rice plant, wheat, barley, corn, bean, potato, Indian bean, oat and Indian millet; vegetable crops such as *Arabidopsis* sp., Chinese cabbage, radish, red pepper, strawberry, tomato, watermelon, cucumber, cabbage, melon, pumpkin, welsh onion, onion and carrot; crops for special use such as ginseng, tobacco plant, cotton plant, sesame, sugar cane, sugar beet, *Perilla* sp., peanut and rape; fruit trees such as apple tree, pear tree, jujube tree, peach tree, kiwi fruit tree, grape tree, citrus fruit tree, persimmon tree, plum tree, apricot tree and banana tree; flowering crops such as rose, gladiolus, gerbera, carnation, chrysanthemum, lily and tulip; and fodder crops such as ryegrass, red clover, orchardgrass, alfalfa, tallfescue and perennial ryograss.

The features and advantages of the present invention will be summarized as follows:

(a) The present invention provides a composition for improving a tolerance to a salt stress or a drought stress of a plant, and a method for preparing transformed plant exhibiting improved tolerance to salt stress or drought stress.

(b) The nucleotide sequences of the present invention are involved in salt or drought stress-tolerance, therefore may be effectively used for cultivating the plants with novel functional features which are less affected by climates and environments of the cultivated areas.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods
Plant Growth Conditions and Sampling

Seeds of the AtSRG1 (At3g49810) and AtSRG2 (At5g65920) knock-out mutants [AtSRG1 seed number: Salk_012549; AtSRG2 seed number: Salk_054774)] which are T-DNA insertion lines were purchased from SIGNAL Salk Institute Genomic Analysis Laboratory (http://signal.salk.edu/).

The seeds of AtSRG1 and AtSRG2 knock-out mutants and the wild type *Arabidopsis thaliana* were soaked in 30% bleach solution (Yuhan-clorox) for 6 min, and washed 5 times with sterilized water. The treated seeds were grown on MS (Murashige and Skoog) medium (Duchefa Biochemie) containing 1% sucrose, B5 vitamin (12 mg/L) and 0.7% agar in a growth chamber for 2 weeks under a condition of continuous light. Where green whole plants of light condition were used as materials, seeds were grown on soil of Sunshine MIX #5 (Sun GroHorticulture) in a growth chamber for 3 weeks (under a condition of continuous light).

Treatments of Stresses (Salt and Drought)

The AtSRG1 (At3g49810) and AtSRG2 (At5g65920) genes were predicted to be induced by a salt stress. In order to confirm these possibilities, the expressions of the AtSRG1 and AtSRG2 genes were analyzed by semi quantitative RT-PCR after treatment of salt and drought.

In order to determine the expressions of the AtSRG1 and AtSRG2 genes to drought stress, the wild type *Arabidopsis thaliana* seedlings which were grown on medium for 2 weeks were exposed in the air, and sampled after 1.5 and 3 hours. To investigate the expressions of the genes under salt stress, the wild type *Arabidopsis thaliana* seedlings which were grown on medium for 2 weeks were treated with 300 mM sodium chloride, and sampled after 1.5 and 3 hours. The sampled tissues were grinded with liquid nitrogen in mortar. The powders were added with 2 ml of an extraction buffer (4 M guanidine-HCl 20 mM, 10 mM EDTA, 10 mM EGTA (USB), 0.5% Sarkosyl (SIGMA), pH 9) per 1 g of the powder and β-mercaptoethanol (SIGMA-ALDRICH) to extract. The extract was transferred to conical tube, suspended with an equal volume of PCI (phenol:chloroform: isoamyl alcohol=25:24:1), vortexed for 5 min and centrifuged at 3,500 rpm for 25 min (Hanil centrifuge, HA-1000-3). After centrifugation, the supernatant of upper organic solvent phase was removed. The extract was resuspended with an equal volume of PCI, vortexed and centrifuged. The extract was performed twice with the process described above. Then, the lower aqueous phase was performed twice with ethanol precipitation and once with LiCl precipitation to isolate RNA.

Quantitative Reverse Transcriptase Polymerase Chain Reaction (RT-PCR)

Total RNA was isolated from leaves of the mutants and the wild-type plants. Single-strand cDNA was synthesized by using RNA with oligo dT primer and MMLV reverse transcriptase (Fermentas). PCR was conducted in the final volume of 20 μL containing 20 ng of cDNA as a template, 10 pmole of each of two types of primers, 2 μL of 10× Taq polymerase buffer (Intron), 2 μL of dNTPs (each of 1.25 mM) and 1 unit of Taq DNA polymerase (Intron). The reaction mixture was placed in Bio-Rad C-1000 thermal cycler. The reaction mixture was denatured for 2 min at 94° C. and subjected to 25 cycles of 20 sec at 94° C., 20 sec at 52° C. and 45 sec at 72° C. After 25 cycles, polymerization was further performed at 72° C. for 4 min. Then, the PCR products were stored at −20° C. in a freezer. The sequences of primers used in this Example are shown in Table 1.

TABLE 1

Primers used in RT-PCR

| primer | sequence | SEQ ID No. |
| --- | --- | --- |
| #AtSRG1 U3 FW | 5'-CAAGCTAGGGTTCATGCTTTG-3' | SEQ ID NO: 5 |
| #AtSRG1 17 RV | 5'-CAGACACCCTCATCAGCACC 3' | SEQ ID NO: 6 |
| #AtSRG2 u5 FW | 5'-GGTCAAACCTACGAGAGGTCC-3' | SEQ ID NO: 7 |
| #AtSRG2 20 RV | 5'-CGATTTGAGCAGCGTTAACG-3' | SEQ ID NO: 8 |

TABLE 1-continued

Primers used in RT-PCR

| primer | sequence | SEQ ID No. |
|---|---|---|
| RD29a FW | 5'-CAGGTGAATCAGGAGTTGTT-3' | SEQ ID NO: 9 |
| RD29a RV | 5'-CCGGAAATTTATCCTCTTCT-3' | SEQ ID NO: 10 |
| EV136F Act8 FW | 5'-TACTGATTACCTCATGAAGATC CTTAC-3' | SEQ ID NO: 11 |
| EV137R Act8 RV | 5'-AAACGATGTCTCTTTAGTTTAG AAGC-3' | SEQ ID NO: 12 |

Extraction of Genomic DNA of Mutants Inserted with T-DNA and Acquisition of Homozygous Mutant The seeds of the wild type *Arabidopsis thaliana* and knock-out mutants were grown on soil for 2 weeks and their leave were grinded with liquid nitrogen in mortar. The powders were added with 700 µl/66 mg of CTAB buffer (2% CTAB, 100 mM Tris pH 8, 20 mM EDTA, 1.4 M NaCl, 2% PVP40), mixed and heated at 65° C. for 10 min. The resultants were added to 570 µl of CI (chloroform:isoamyl alcohol=24:1), mixed and vortexed for 5 min followed by centrifugation at 13,000 rpm for 10 min. After centrifugation, 300 µl of the supernatant was transferred to EP tube and washed with 70% ethanol, dried. The obtained genomic DNA was dissolved in water to use. Genotyping PCR was performed using T-DNA border primer (LBa1) and primers annealing to sites upstream and downstream of the T-DNA insertion site.

TABLE 2

Primers used in Genotyping PCR and RT-PCR

| primer | sequence | SEQ ID No. |
|---|---|---|
| #AtSRG1 u3 FW | 5'-CAAGCTAGGGTTCATGCTTTG-3' | SEQ ID NO: 5 |
| #AtSRG1 u4 RW | 5'-TCCCAATGCTTATTGCAAAAC-3 | SEQ ID NO: 13 |
| #AtSRG2 u5 FW | 5'-GGTCAAACCTACGAGAGGTCC-3' | SEQ ID NO: 7 |
| #AtSRG1 u6 RW | 5'-ATCCGTTGTGTGATTTTGACC-3' | SEQ ID NO: 14 |
| LBa1 border primer | 5'-TGGTTCACGTAGTGGGCCATCG-3' | SEQ ID NO: 15 |

Measurement of Sensitivity to Salt Stress in Germination Stage

The seeds of AtSRG1 (At3g49810) and AtSRG2 (At5g65920) knock-out mutants and the wild type were soaked in 30% bleach solution (Yuhan-clorox) for 6 min, and washed 5 times with sterilized water. The treated seeds were grown on MS (Murashige and Skoog) medium (Duchefa Biochemie) containing 1% sucrose, B5 vitamin (12 mg/L) and 0.7% agar, with or without 50 mM, 100 mM, 125 mM, 150 mM and 175 mM NaCl, followed by imbibition in 4° C. chamber (dark condition), and then the sensitivity to salt stress was observed in growth chamber (continuous light).

Measurement of Sensitivity to Drought Stress in Mature Plants

The seeds of AtSRG1 (At3g49810) and AtSRG2 (At5g65920) knock-out mutants and the wild type *Arabidopsis thaliana* were grown on soil of Sunshine MIX #5 (Sun GroHorticulture) in a growth chamber for 3 weeks (continuous light). The plants were supplied with water containing 200 mM, 250 mM and 300 mM NaCl every 3 days, and then supplied with water without NaCl after 2 days. High salt-tolerance was evaluated through chlorosis of shoot.

Results

Gene Expression after Salt and Drought Stress Treatments

The expression patterns of AtSRG1 (At3g49810) and AtSRG2 (At5g65920) under salt and drought stresses were analyzed by semi-quantative RT-PCR. After treatments of salt stress, AtSRG1 mRNA and AtSRG2 mRNA expression levels in root tissue were increased (FIG. 1). Drought stress also induced mRNA expression in root, though not as much as salt stress did (FIG. 1). Considering the similar patterns of two genes under salt and drought stresses, it is inferred that these two genes may have functions complementary to each other.

Measurement of Sensitivity to Salt Stress at Germination Stages

For concrete approach to the physiological functions of AtSRG1 (At3g49810) and AtSRG2 (At5g65920) genes, the phenotype of the knock-out mutants and the wild type were analyzed after high salt treatment. At first, seeds obtained from the AtSRG1 knock-out mutant and the wild type *Arabidopsis thaliana* were seeded on media with or without NaCl (FIGS. 3a-3d). As results, it was revealed that the high salt-resistance was enhanced in knock-out mutant, and that the high salt-resistance was maintained after germination. These results indicate that the AtSRG1 gene is involved in the response of a plant to salt stress at germination stage.

Measurement of Sensitivity to Drought Stress in Mature Plants

Figure 4:
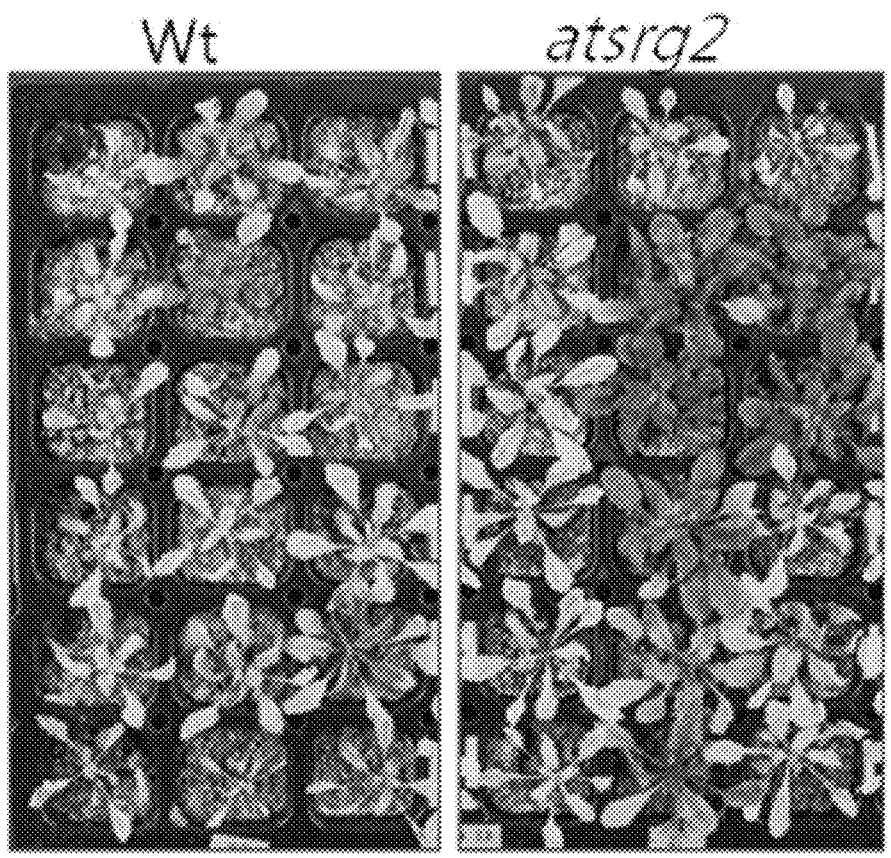
FIG. 4 represents the phenotypes of AtSRG2 knock-out mutants in response to high salt in green plants. After analyzing the phenotypes of AtSRG1 knock-out mutants, it was examined whether AtSRG2 knock-out mutant also had high salt-resistance. Contrary to the experiments indicated in FIG. 3*d* where high salt is added at the seed stage, NaCl is treated to 3-week-old plants for 2 weeks.

To investigate the tolerance of mature mutant plants, salt stress were subjected to previously prepared wild type and knock-out mutant plants. 3-week-old AtSRG1 (At3g49810 and AtSRG2 (At5g65920) knock-out mutants and the wild type *Arabidopsis thaliana* were treated with 200 mM, 250 mM and 300 mM of NaCl solutions every 3 days. After 3 days, the plants were supplied with plain water. Phenotypes of the plants were analyzed 2 weeks after salt treatment (FIG. 4). As results, AtSRG2 knock-out mutants were found to have strong tolerance to high salinity.

Phenotype analysis at germination stage and mature plant stage demonstrated that AtSRG1 (At3g49810) and AtSRG2 (At5g65920) genes are involved in the response to a salt stress at early stages of germination and at green plants, respectively, and that dual knock-out of these genes may confer enhanced salt-tolerance during overall period since germination.

Having described a specific embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for preparing transformed *Arabidopsis thaliana* exhibiting improved tolerance to a salt stress, the method comprising:
    (a) introducing a transformation vector into the AtSRG1 gene, wherein the transformation vector inhibits an expression of a nucleotide sequence encoding the amino acid sequence consisting of SEQ ID NO:3 into a *Arabidopsis thaliana* cell;
    (b) obtaining the transformed *Arabidopsis thaliana* exhibiting improved salt stress tolerance from the *Arabidopsis thaliana* cell of (a); and
    (c) growing the transformed *Arabidopsis thaliana* under a salt stress condition.

2. A method for improving a tolerance to a salt stress of *Arabidopsis thaliana*, the method comprising:
    (a) introducing a transformation vector into the AtSRG1 gene, wherein the transformation vector inhibits an expression of a nucleotide sequence encoding the amino acid sequence consisting of SEQ ID NO:3 into a cell of the *Arabidopsis thaliana*;
    (b) obtaining a transgenic *Arabidopsis thaliana* exhibiting improved tolerance to a salt stress from the cell of the *Arabidopsis thaliana*; and
    (c) growing the transgenic *Arabidopsis thaliana* under a salt stress condition.

3. The method according to claim 2, wherein the nucleotide sequence encoding the amino acid sequence of SEQ ID NO:3 is the nucleotide sequence of SEQ ID NO:1.

4. The method according to claim 2, wherein the transformation vector is T-DNA.

5. The method according to claim 1, wherein the nucleotide sequence encoding the amino acid sequence of SEQ ID NO:3 is the nucleotide sequence of SEQ ID NO:1.

6. The method according to claim 1, wherein the transformation vector is T-DNA.

* * * * *